United States Patent [19]
Ryan

[11] Patent Number: 5,376,140
[45] Date of Patent: Dec. 27, 1994

[54] PROSTHETIC FOOT

[76] Inventor: Michael W. Ryan, 2935 Telegraph Ave., Berkeley, Calif. 94705

[21] Appl. No.: 946,836

[22] Filed: Sep. 21, 1992

Related U.S. Application Data

[63] Continuation-in-part of Ser. No. 816,490, Jan. 3, 1992, abandoned.

[51] Int. Cl.⁵ ............................................. A61F 2/66
[52] U.S. Cl. ........................................ 623/55; 623/53
[58] Field of Search ................................ 623/53–56, 623/50, 48–49

[56] References Cited

U.S. PATENT DOCUMENTS

| | | | |
|---|---|---|---|
| 2,453,969 | 11/1948 | Carter | 623/53 X |
| 3,754,286 | 8/1973 | Ryan | 623/55 X |
| 4,652,266 | 3/1987 | Truesdell | 623/55 |
| 5,115,384 | 5/1992 | Wilson et al. | 623/49 |
| 5,156,632 | 10/1992 | Wellershaus | 623/55 |

FOREIGN PATENT DOCUMENTS 2640499  6/1990  France ................................ 623/53

Primary Examiner—Randall L. Green
Assistant Examiner—D. Willse
Attorney, Agent, or Firm—Howard Cohen

[57] ABSTRACT

An improved prosthetic foot construction providing resilient lateral flexion as well as excellent longitudinal flexion and energy recovery includes a core frame embedded in an expanded polymer body that mimics the shape of a natural foot. The core frame extends in a generally vertical plane, and comprises a modified trapezoidal shape having an open medial region. The frame includes an upper side having a mounting bolt extending therethrough to a lower leg prosthesis, and a lower side generally parallel to the sole of the prosthesis. The rear side of the trapezoid extends generally parallel to the rear heel surface of the prosthesis, and the front side extends obliquely from the upper side toward the lower side. A ball and socket connection joins the front side and the lower side of the frame, so that the oblique front side of the frame may undergo rotational motion with respect to the remainder of the frame. As a result, the top side may be driven into lateral flexion with respect to the frame and the foot to provide resilient lateral flexion of the foot and duplicate the flexibility of a natural ankle. The core frame is formed of a high density polymer material reinforced with carbon fiber extending continuously thereabout from the toe end of the lower side of the frame to the ball and socket interface at the lower end of the oblique front side of the frame, adding significant strength and resiliency to the frame, increasing its efficiency in returning energy to the user and enhancing the longevity of the prosthesis. The frame is cast in place within the foamed polymer body of the prosthetic foot. The core frame does not extend to the toe region of the body, so that the toe region may undergo elastic flexion during the plant and toe roll-off stages of stepping, thus providing highly efficient energy recovery for walking, running, and the like.

11 Claims, 4 Drawing Sheets

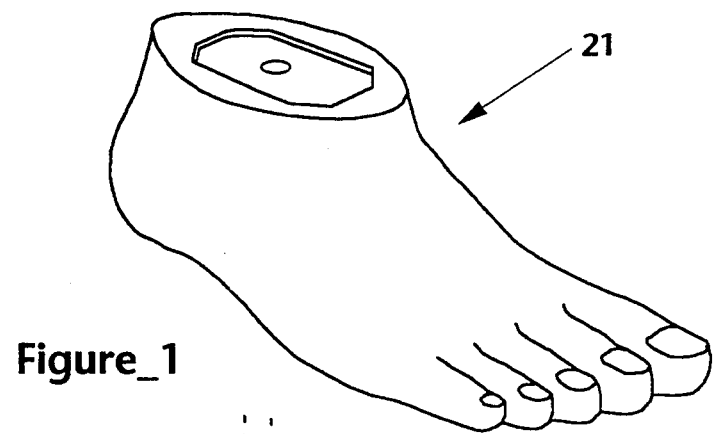
Figure_1
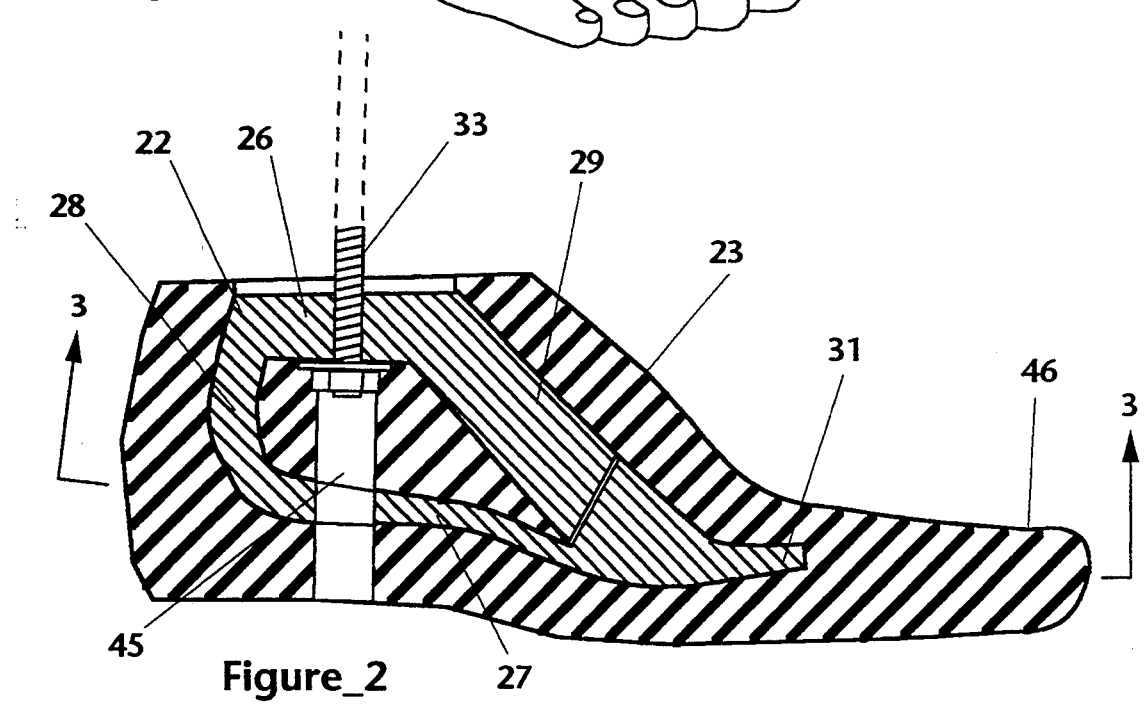
Figure_2
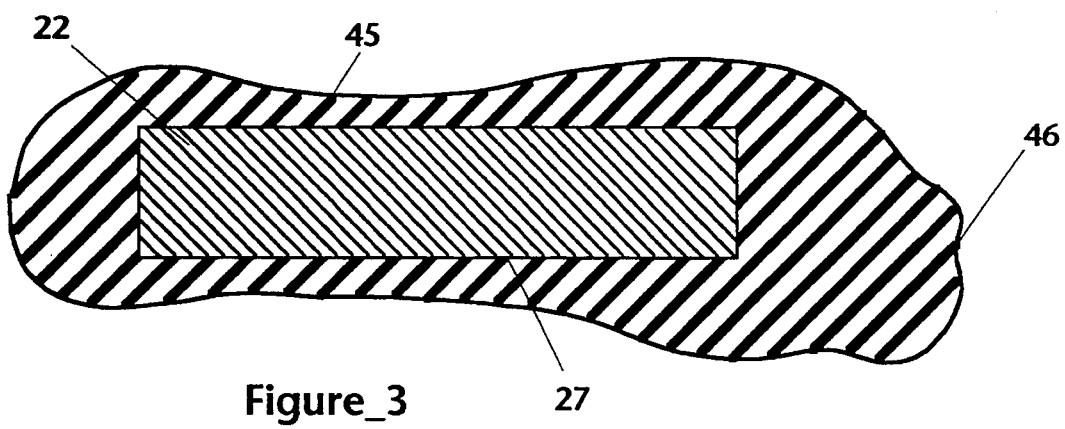
Figure_3

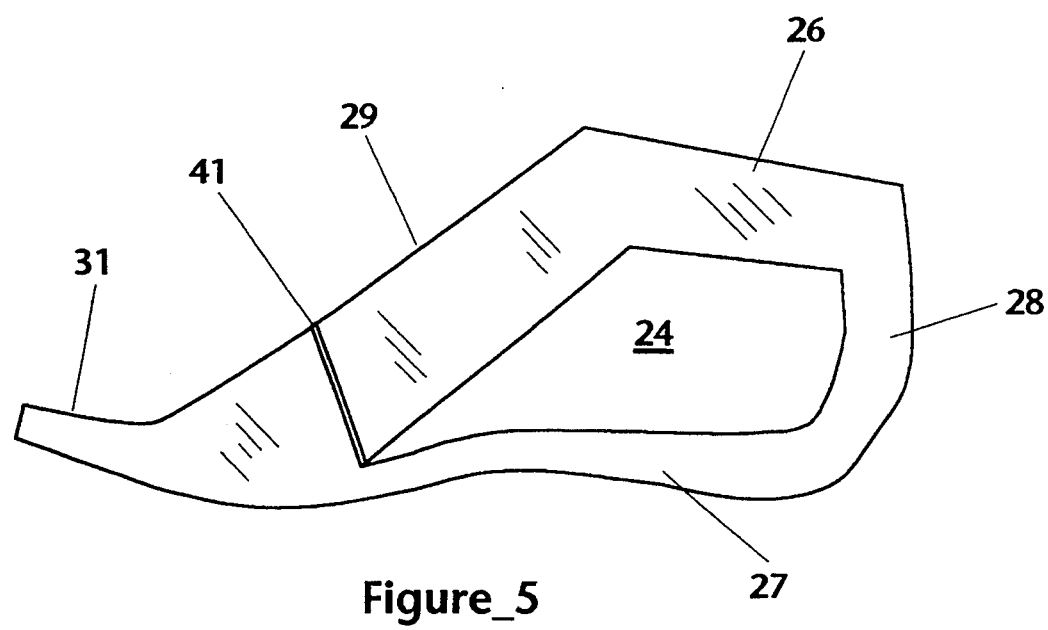
Figure_5
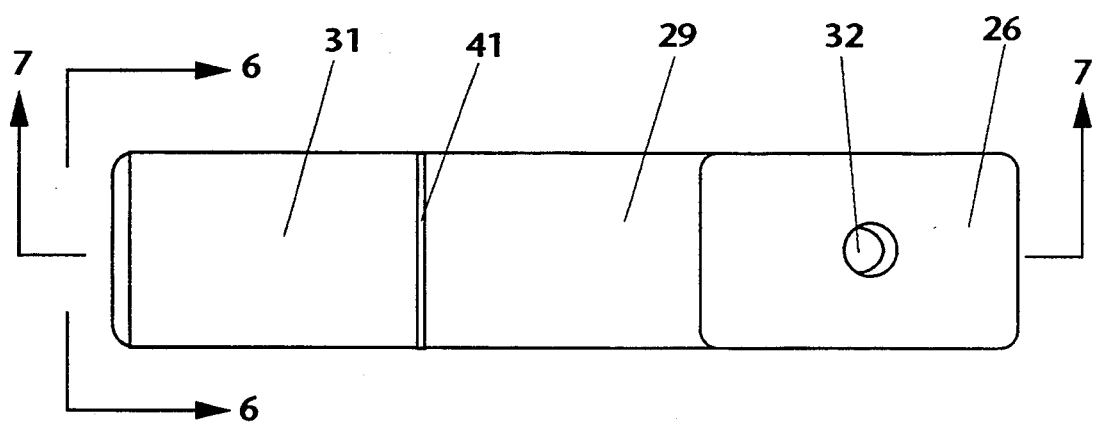
Figure_4
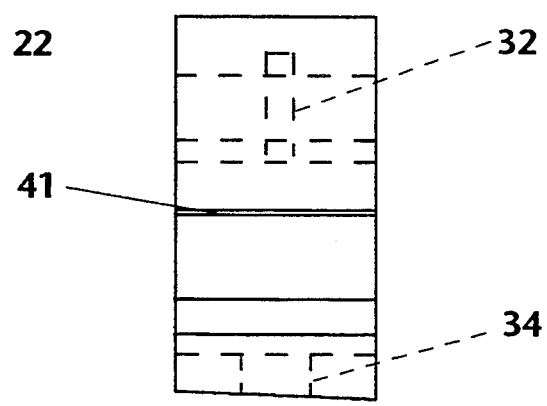
Figure_6

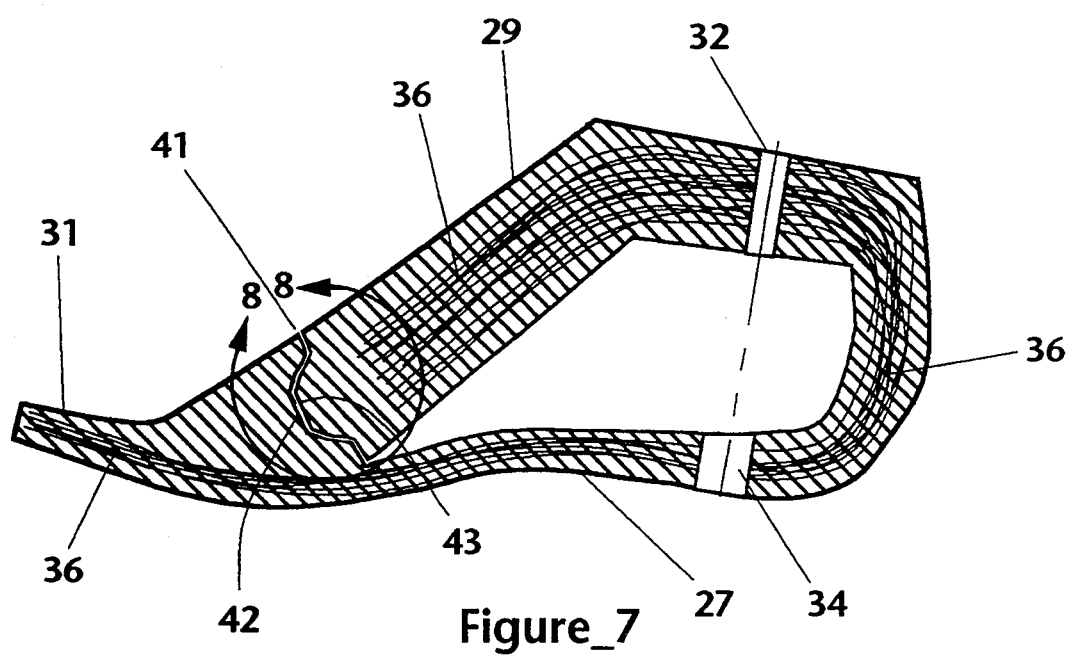
Figure_7
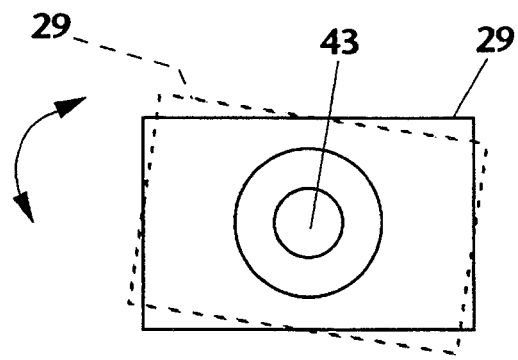
Figure_8
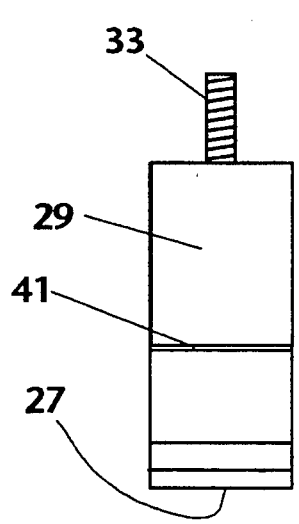
Figure_9a
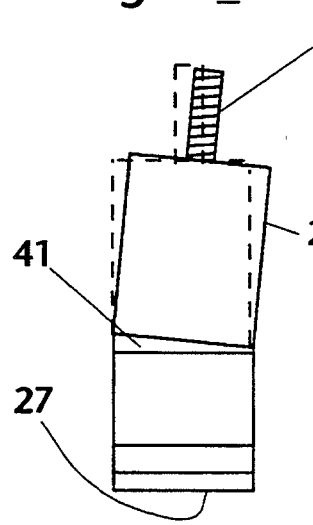
Figure_9b
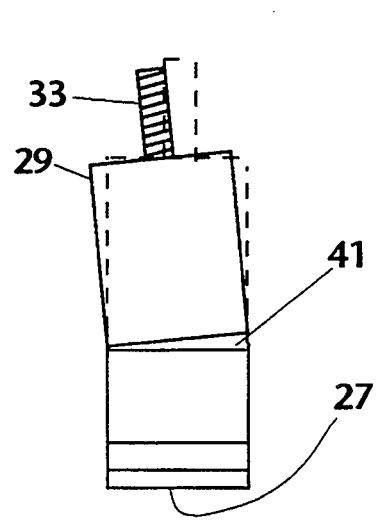
Figure_9c

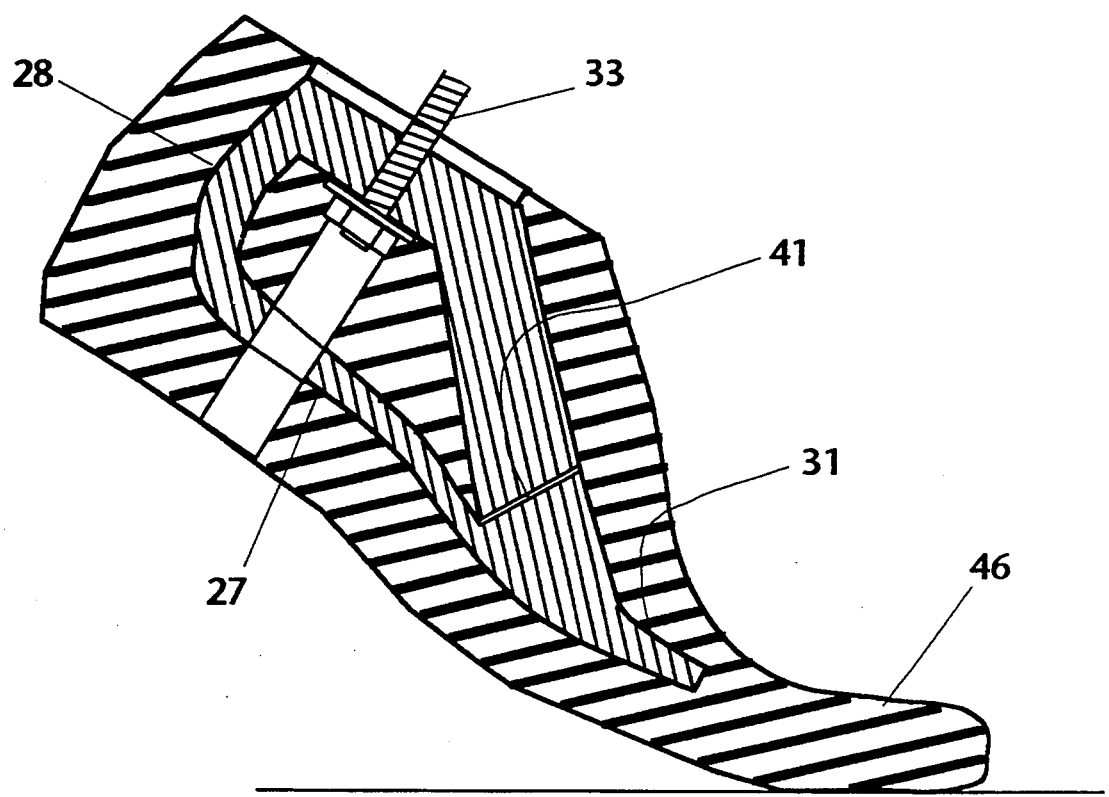
Figure_10
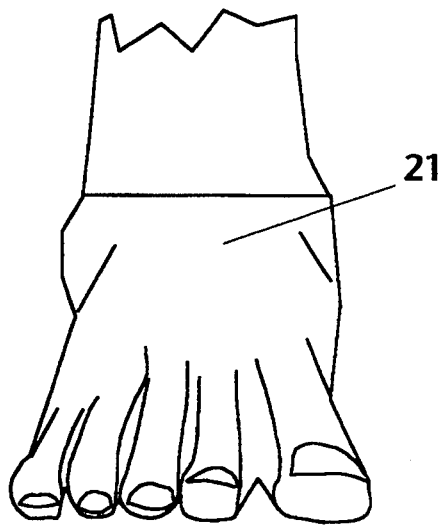
Figure_11
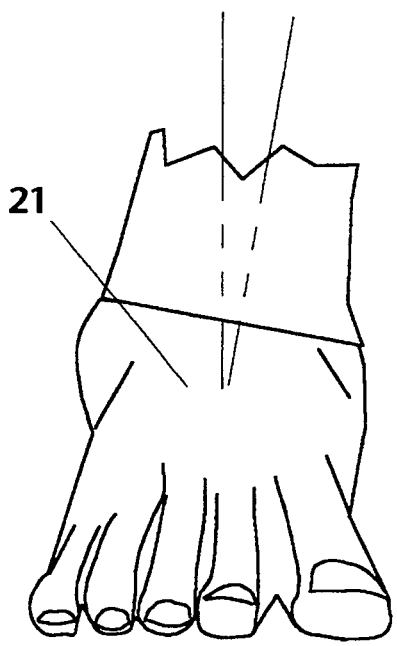
Figure_12

PROSTHETIC FOOT

REFERENCE TO RELATED APPLICATION

This application is a continuation-in-part of U.S. patent application Ser. No. 07/816,490, filed Jan. 3, 1992, now abandoned by Michael Ryan, for which priority is claimed.

BACKGROUND OF THE INVENTION

In the development of a prosthetic foot for amputees, the SACH (solid ankle, cushion heel) foot innovation was considered a benchmark in modern prosthesis for its comfort and energy conservation. The original SACH concept has been modified in the ensuing decades by providing various forms of articulated keels to increase energy return, as well as using modern polymer and expanded polymer materials to increase comfort. The purpose of a flexible, elastic keel is to store energy during the foot-flat and rollover portions of the walking movement, followed by releasing of energy from the keel during the toe-off motion.

Several deficiencies have been noted in these prosthetic feet, even though they have achieved user acceptance. One major problem is that many of the prosthetic foot constructions include precision machined components that are expensive to manufacture and contribute to a high unit cost. Moreover, the metal components, which are generally embedded in a cast polymer or expanded polymer body, are not compatible with the polymer material on a long-term basis. That is, the polymer or expanded polymer material is much more resilient and flexible than the metal (typically steel, aluminum, or brass), and the constant flexion of the prosthetic foot during use leads to delamination of the interface between the metal components and the polymer-based material. Thus the prostheses tended to wear out after a relatively short period.

More significantly, prior art prosthetic feet have been designed with a focus on longitudinal flexion for energy recovery in a forward walking motion on a level surface. However, these devices have poor performance in lateral flexion motion, since the need for such flexure was not recognized in the prior art. Lateral flexion is required for many actions, due to the fact that real-world activities take place on sidewalks or roadways that are uneven and not level, and that obstacles such as curbs, broken pavement, and the like are often encountered. Due to the fact that prior art prosthetic feet have not been able to undergo lateral flexion, there has been painful wear and tear on the amputees' stumps from simple daily activities as well as running, jumping, dancing and the like.

SUMMARY OF THE PRESENT INVENTION

The present invention generally comprises an improved prosthetic foot construction that is simpler and more natural than prior art devices. A salient feature of the invention is that is provides resilient lateral flexion while also providing excellent longitudinal flexion and energy recovery. A further aspect of the invention is that it is free of metal components and machined components, so that cost is minimized and longevity of the prosthesis is maximized.

The prosthetic foot includes a core frame embedded in an expanded polymer body that mimics the shape of a natural foot. The core frame extends in a generally vertical plane, and comprises a modified trapezoidal shape having an open medial region. The modified trapezoidal shape includes an upper side having a mounting bolt extending therethrough to an ankle or lower leg prosthesis, and a lower side generally parallel to the sole of the prosthesis. The rear side of the trapezoid extends generally parallel to the rear heel surface of the prosthesis, and the front side extends obliquely from the upper side toward the lower side. A significant feature of the core frame is that the front side thereof is not connected fixedly to the lower side. Rather, there is provided a ball and socket connection between the front side and the lower side of the frame, so that the oblique front side of the frame may undergo torsional motion with respect to the remainder of the frame. As a result, the top side may be driven into lateral flexion with respect to the frame and the foot to provide resilient lateral flexion of the foot and duplicate the flexibility of a natural ankle.

A significant feature of the core frame is that is formed of a high density polymer material, and that it includes reinforcing carbon fiber extending continuously thereabout from the too end of the lower side of the frame to the ball and socket interface at the lower end of the oblique front side of the frame. The carbon fiber adds significant strength and resiliency to the frame, increasing its efficiency in returning energy to the user and enhancing tile longevity of the prosthesis.

The core frame is cast in place within the foamed polymer body of the prosthetic foot, so that the foam polymer material encases the core frame and also fills the hollow medial region thereof. The bond between the polymer material of the core frame and the expanded polymer of the body is extremely strong, so that the prosthesis lasts for a very long time. The core frame does not extend to the toe region of the body, so that the toe region may undergo elastic flexion during the plant and toe roll-off stages of stepping, thus providing highly efficient energy recovery for walking, running, and the like. Moreover, the foam polymer material provides a highly cushioned prosthesis that is very comfortable and gentle to the stump of the amputee.

BRIEF DESCRIPTION OF THE DRAWING

FIG. 1 is a perspective view of the prosthetic foot of the present invention.

FIG. 2 is a cross-sectional side view of the prosthetic foot of the present invention.

FIG. 3 is a cross-sectional view of the prosthetic foot, taken along line 3—3 of FIG. 2.

FIG. 4 is a top view of tile core frame of the prosthetic foot of the present invention.

FIG. 5 is a side elevation of the core frame shown in FIG. 4.

FIG. 6 is a front view of the core frame, taken along line 6—6 of FIG. 4.

FIG. 7 is a cross-sectional elevation of the core frame of the invention, taken along line 7—7 of FIG. 4.

FIG. 8 is an enlarged detail view of the ball and socket feature of the core frame, taken along line 8—8 of FIG. 7.

FIGS. 9a, 9b, and 9c are a sequence of front elevations of the core frame, showing the lateral flexion of the core frame.

FIG. 10 is a cross-sectional elevation of the prosthetic foot of the invention, shown in a toe-plant disposition.

FIG. 11 is a front view of the prosthetic foot of the invention, shown connected to a lower leg prosthesis.

FIG. 12 is front view of the invention as in FIG. 10, showing the lateral flexion facilitated by the construction of the present invention.

DESCRIPTION OF THE PREFERRED EMBODIMENT

The present invention generally comprises an improved prosthetic foot. With regard to FIGS. 1-3, the prosthetic foot 21 is comprised of two major components: a core frame 22 and a surrounding body 23. The core frame 22 provides the structural strength and stiffness required for the prosthesis, and the body 23 provides the cushioning and resilience required for the comfort of the riser.

With regard to FIGS. 2-6, the core frame 22 is configured as a modified trapezoid extending in a generally vertical plane within the prosthesis. The trapezoid includes an open medial region 24, upper and lower sides 26 and 27, respectively that are slightly offset from a parallel relationship. The rear side 28 of the trapezoid extends generally parallel to the rear heel surface of the prosthesis, joining the upper and lower sides 26 and 27. A front side 29 extends obliquely downwardly from the top side 26 toward the toe portion 31 of the core frame.

All of the sides have a rectangular cross-section of constant width, with the upper side and front side having thicker cross-sections for increased strength and stiffness. The core frame is approximately 1.5 inches wide and approximately 6-7 inches long for an average size prosthesis. The upper side 26 of the frame includes a hole 32 extending vertically therethrough to receive a mounting bolt or stud 33 for joining the prosthetic foot 21 to a leg prosthesis. An access hole 34 extends through the lower side 27 in axial alignment with the hole 32 to provide mechanical access to the inner end of the bolt 33.

The core frame is formed of a polymer material that is strong and resilient, such as thermoplastic polyester elastomer having a durometer hardness of 40 D to 72 D. With reference to FIG. 7 in particular, a salient feature of the core frame is that it is reinforced with carbon fiber 36 or the like disposed within the polyester elastomer and cast in place as the material is polymerized. The carbon fiber extends continuously from the toe portion 31 through the lower side 27, around the access hole 34, through the rear side 36, top side 26, and front side 29 to the lower end thereof. The carbon fiber adds significant strength and elasticity to the core frame, enhancing the amount of energy that is returned from the frame during flexure and extending the life of the prosthesis by preventing the propagation of cracks and faults in the polymer material of the frame.

A further significant feature of the invention is that the front side 29 of the frame is joined to the toe portion 31 by a ball and socket connection 41. As shown in FIGS. 7 and 8, the connection 41 includes confronting surfaces of the front side 29 and the toe portion 31, with a concave depression 42 formed in the confronting surface of the toe portion and a ball-like protrusion 43 formed in the confronting surface of the front side. The intrinsic stiffness and resilience of the core frame maintains the ball protrusion 43 within the socket depression 42, and a PTFE surface is provided to minimize friction between the mating surfaces.

The ball and socket connection 41 is capable of transmitting vertical and longitudinal loads from the front side 29 to the toe portion 31, due to the planar portions of the confronting surfaces, while at the same time permitting relative rotational motion between the front side 29 and the toe portion 31, as shown in FIG. 8. The rotational freedom provided by the ball and socket connection 41 is resisted by the elastic torsional stiffness of the core frame 22, and it is sufficient to provide lateral flexion to the prosthesis. As a result, as shown in FIGS. 9a-9c, the upper side and the mounting bolt 33 (joined to the leg prosthesis) may undergo substantial lateral rotation with respect to the bottom side 27 of the core frame 22. This lateral rotation is important in accommodating such positions as standing on a non-horizontal surface, stepping on an object like a rock or a structure like a curb that causes the foot to tilt laterally, or activities such as sports, dancing, or the like that require lateral flexure.

The body portion 23 of the prosthesis 21 is formed of a resilient expanded polymer material such as polyurethane foam or the like cast in the shape of a natural foot. An access hole 45 extends into the bottom surface of the body portion in alignment with the hole 34 of the frame to provide access to the inner end of the bolt 33. The material of the body is substantially softer, more elastic, and less stiff than the core frame material, and completely surrounds the core frame and also fills the open medial region 24 thereof. As shown in FIGS. 2 and 3, the toe portion 31 of the core frame does not extend to the toe portion 46 of the body 23. As a result, as shown in FIG. 10, the toe portion 46 of the body 23 is much more flexible and resilient that the remainder of the prosthesis. With reference to FIG. 10, the toe portion of the body flexes easily during the toe plant portion of a step, and the expanded polymer material is very efficient in returning the energy of the toe flexure to propel the individual forward. The softness and resilience of the expanded polymer also acts to cushion the impact of heel plant during walking and running, so that the amputee's stump is buffered from the shock of walking and running. Likewise, the polymer foam is sufficiently resilient to permit the lateral flexure of the frame 22, so that the prosthetic foot can roll laterally to accommodate everyday motions, as shown in comparing the upright position of FIG. 11 and the lateral flexed position of FIG. 12.

It should be noted that the prosthetic foot of the invention provides excellent energy return during walking, running, and the like, as well as lateral flexion, without recourse to any mechanism other than the solid-state structure disclosed herein. Moreover, due to the fact that the polymer material of the core frame and the expanded polymer material of the body are well bonded and fully compatible, the assembly forming the prosthesis exhibits little wear during use and retains its usefulness far longer than prior art prosthetic feet.

I claim:
1. A prosthetic foot, including:
 a mass of resilient flexible elastomer formed into the general shape of a human foot;
 a polymer core frame contained in said mass and bonded thereto, said core frame including a plurality of sides extending contiguously to define an open medial region with a closed perimeter defined by said plurality of sides, said flexible elastomer extending into and filling said open medial region;
 means for securing said core frame to a prosthetic leg, whereby vertical weight loads, longitudinal compressive loads and lateral torsional loads are transmitted from the prosthetic leg to said core frame; and rotatable connection means for rotatably joining an upper portion of said core frame to a lower portion of said core frame to transfer said longitudinal compressive loads from said upper portion to said lower portion and to decouple said lateral torsional loads between said upper portion and said lower portion.

2. The prosthetic foot of claim 1, wherein said plurality of sides include upper and lower sides, a rear side, and an oblique side disposed to define a modified trapezoidal configuration.

3. The prosthetic foot of claim 2, wherein said means for securing said core frame to a prosthetic leg includes a threaded component secured to said upper side of said core frame and extending upwardly therefrom.

4. The prosthetic foot of claim 3, further including an access hole extending from a lower surface of said mass into said frame to an inner end of said threaded component.

5. The prosthetic foot of claim 1, wherein said plurality of sides include upper and lower sides, a rear side, and an oblique side disposed to define a modified trapezoidal configuration, said oblique side, upper side, rear side, and lower side extending continuously, and said rotatable connection means extending between confronting portions of said oblique side and said lower side.

6. The prosthetic foot of claim 5, wherein said rotatable connection means includes confronting surfaces of said oblique side and said lower side, a ball-like protrusion extending from one of said confronting surfaces, and a concave socket formed in the other of said confronting surfaces and dimensioned to receive said protrusion.

7. The prosthetic loot of claim 5, wherein said core frame includes a toe portion extending forwardly from a forward end of lower side.

8. The prosthetic foot of claim 7, further including fiber reinforcing means disposed within said core frame, said fiber reinforcing means including a plurality of fibers extending generally continuously from said toe portion through said lower side, said rear side, said upper side, and said oblique side to said rotatable connection means.

9. The prosthetic foot of claim 7, wherein said mass includes a toe region corresponding to the toe region of a natural foot, said toe region of said mass being free of said toe portion of said core frame.

10. The prosthetic foot of claim 7, wherein said sides all have rectangular cross-sectional configurations of generally similar width and varying thickness.

11. The prosthetic foot of claim 10, wherein said upper and oblique sides have cross-sectional configurations that are thicker than the cross-sectional configurations of the rear and lower sides.

* * * * *